United States Patent [19]

Vincent et al.

[11] Patent Number: 4,959,372

[45] Date of Patent: Sep. 25, 1990

[54] ANTI-HYPERTENSIVE SUBSTITUTED 2-AZABICYCLOOCTANE-3-CARBOXYLIC ACIDS

[75] Inventors: Michel Vincent, Bagneux; Georges Remond, Versailles; Michel Laubie, Vaucresson, all of France

[73] Assignee: Adir Et lie, Neuilly-sur-Seine, France

[21] Appl. No.: 237,497

[22] Filed: Aug. 26, 1988

[30] Foreign Application Priority Data

Aug. 28, 1987 [FR] France ................................. 87 12013

[51] Int. Cl.$^5$ ..................... A61K 31/44; C07D 471/08
[52] U.S. Cl. ..................................... 514/299; 546/112
[58] Field of Search ....................... 546/112; 514/299

[56] References Cited

U.S. PATENT DOCUMENTS

| 4,397,857 | 8/1983 | Vincent et al. | 546/112 |
| 4,472,380 | 9/1984 | Harris et al. | 514/2 |

FOREIGN PATENT DOCUMENTS

| 0105102 | 4/1984 | European Pat. Off. |
| 0051020 | 8/1984 | European Pat. Off. |
| 3227055 | 1/1984 | Fed. Rep. of Germany |

OTHER PUBLICATIONS

Patchett et al., Nature, vol. 288, pp. 280–283 (1980).

*Primary Examiner*—Mary C. Lee
*Assistant Examiner*—Bernard L. Dentz
*Attorney, Agent, or Firm*—Gordon W. Hueschen

[57] ABSTRACT

Compounds of formula (I):

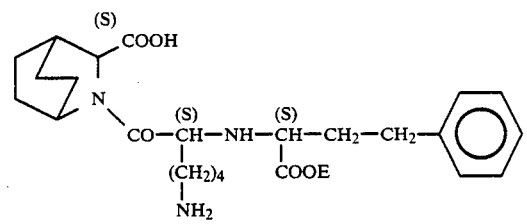

in which E denotes a lower alkyl group, or preferably a hydrogen atom, and their addition salts with a pharmaceutically acceptable acid or base, the preparation thereof and pharmaceutical compositions containing them.

6 Claims, No Drawings

ANTI-HYPERTENSIVE SUBSTITUTED 2-AZABICYCLOOCTANE-3-CARBOXYLIC ACIDS

The present invention relates to new compounds of 2-azabicyclooctane-3-carboxylic acid, to methods for the preparation thereof and to pharmaceutical compositions containing them.

More specifically, the present invention relates to the compounds of formula (I):

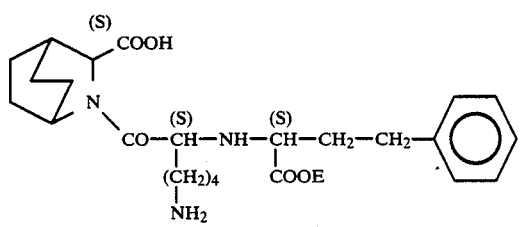

in which E denotes a lower alkyl group, or preferably a hydrogen atom,
as well as their addition salts with a pharmaceutically acceptable acid or base.

European Patent No. 0,051,020 is known, which patent claims compounds of general formula (II):

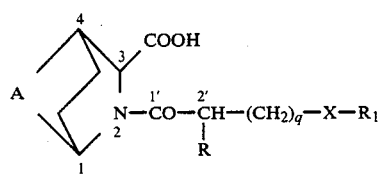

in which A denotes a vinylene or dimethylene radical,
q is 0 or 1,
R denotes a lower alkyl radical capable of bearing an amino group,
X denotes —S— and $R_1$ denotes H, or alternatively X denotes —NH— and
$R_1$ denotes a hydrogen atom or a radical of formula:

where $R_2$ denotes a hydroxyl or a lower alkoxy group and $R_3$ denotes, in particular, a hydrogen atom, or a linear or branched alkyl, cycloalkyl or phenylalkyl radical, having at most and in total 8 carbon atoms, the expressions alkyl or lower alkoxy radicals meaning groups having from 1 to 4 carbon atoms.

The preferred compounds of European Patent No. 0,051,020 have a methyl group as the meaning of R (page 2, line 58).

The compounds of formula (I) are hence special cases of the derivatives of formula (II) for which R denotes a 4-aminobutyl group. The compounds of the formula (I) are hence not the preferred compounds of European Patent No. 0,051,020.

The Applicant has, in effect, discovered that the compound of formula (I) for which E denotes a hydrogen atom possesses an inhibitory activity with respect to the enzyme for conversion of angiotensin I to angiotensin II, the level and duration of action of which are surprising and markedly superior to those of the preferred compounds of European Patent No. 0,051,020. Thus, when administered orally at a dose of 1 mg.kg$^{-1}$, the derivative of formula (I) for which E=H induces, very rapidly after its administration, a very high percentage-inhibition of the converting enzyme (80%, 15 minutes after administration, in the region of 100%, only 30 minutes after its administration), a very high level of activity being maintained for a long time after the administration since the percentage inhibition of the converting enzyme remains greater than 70%, 6 hours after the administration. Such a dose, administered orally, of one of the compounds of European Patent No. 0,051,020 does not make- it possible to obtain an activity which is, at the same time, as intense, rapid and long-lasting.

The intensity of the activity, when administered orally, possessed by the compound of the present invention for which E is a hydrogen atom is all the more unexpected for the fact that this compound possesses a diacid structure.

In effect, the compounds specifically claimed in European Patent No. 0,051,020 for which X is NH have an ester structure in respect of the side chain (claims 6 and 7).

The diacid structure is effectively, in general, unfavorable to good oral absorption; the compounds of diacid structure hence have a therapeutic activity of low intensity after administration by this route. These derivatives are hence generally reserved for intravenous administration, where their speed of action is advantageous.

Moreover, it is known that the esterification of the carboxylic acid group of the side chain improves the lipophilic nature of the molecule, and hence facilitates its absorption after oral administration. However, this ester group must then be hydrolyzed in the living body, by specific enzymes, in order to be able to liberate the diacid, which alone possesses therapeutic efficacy. This explains why, in general in the converting enzyme inhibitors of the prior art—and more especially in the derivatives of Patent No. 0,051,020—intended for oral administration, the carboxylic acid group is esterified.

Nevertheless, this ester structure possesses a drawback: the time required by the body for hydrolyzing the ester group of the side chain to acid delays the onset of an intense activity.

With the compound of the present invention for which E is a hydrogen atom, the drawbacks inherent in the diacid structure and also in the ester structure have disappeared, and give place only to the advantages possessed by both structures. In effect, the derivative of the present invention for which E=H is especially well absorbed after oral administration, as attested by the intensity of its action after administration by this route. In addition, this compound has retained the advantages of the diacid structure since, a very short time after its administration, it exhibits an intense activity (80% inhibition of the converting enzyme only 15 minutes after its administration).

In consequence of these factors, the compound of the present invention for which E is a hydrogen atom is very clearly distinguished from the compounds of the prior art for its use in therapy.

However, the invention also relates to the compounds for which E is a lower alkyl radical since, by virtue of the foregoing, these compounds are prodrugs of the compound for which E is a hydrogen atom.

The invention also relates to the addition salts of the compounds of formula (I) obtained with a therapeutically compatible inorganic or organic base or acid.

Among acids which may be added to the compounds of formula (I) to form an addition salt, there may be mentioned, by way of example, hydrochloric, sulfuric, phosphoric, tartaric, malic, maleic, fumaric, oxalic, methanesulfonic, ethanesulfonic, camphoric and citric acids, and the like.

As bases capable of salifying the compounds of formula (I), sodium, potassium, calcium or aluminum hydroxides, alkali metal or alkaline earth metal carbonates or organic bases such as triethylamine, benzylamine, diethanolamine, tert-butylamine, dicyclohexylamine and arginine, and the like, may be used.

The compounds of formula (I), and also their salts, possess advantageous pharmacological properties. They exert, in particular, an inhibitory activity with respect to certain enzymes, such as carboxypolypeptidases, encephalinases or kininase II. They inhibit, in particular, the conversion of the decapeptide angiotensin I to the octapeptide angiotensin II, responsible in some cases for arterial hypertension, by acting on the converting enzyme.

The use of these compounds in therapy hence enables the activity of these enzymes responsible for hypertensive disease or for cardiac insufficiency to be reduced or even abolished. The action of kininase II results in an increase in circulating bradykinin, and also a fall in the arterial blood pressure.

The compounds of the present invention are not only useful in the treatment of hypertension, but also usable for treating acute and chronic cardiac insufficiency, in the treatment of secondary hyperaldosteronism, in the treatment of primary and secondary pulmonary hypertension, in glaucoma, in renal insufficiency, in renal vascular hypertension, and in the treatment of peripheral vascular disorders such as migraine, Raynaud's disease, atherosclerosis, thrombosis, arteritis of the lower limbs, cirrhosis and ascites. Moreover, the compounds of the present invention also possess an inhibitory activity with respect to encephalinase, and can hence have use as an analgesic or anti-inflammatory.

The invention also extends to the pharmaceutical compositions containing, as active principle, a compound of general formula (I) or one of its addition salts with an inorganic or organic base or acid, in combination with one or more non-toxic inert excipients suitable for pharmaceutical use and/or a binding agent, a flavoring agent, a disintegrating agent, a sweetening agent, a lubricant or alternatively a liquid vehicle suitable for intravenous administration, such as pyrogen-free sterile water.

Among the pharmaceutical compositions of the invention, there may be mentioned more especially, those which are suitable for oral, parenteral, ocular, per- or transcutaneous, nasal, rectal, perlingual or respiratory administration, and in particular injectable preparations, aerosols, eye or nose drops, tablets, sublingual tablets, gelatin capsules, capsules, pills, sublingual preparations, suppositories, creams, ointments and gels, and the like.

The pharmaceutical compositions according to the invention can, in addition, contain another active principle having a synergistic or complementary action.

Among the latter active principles, there may be mentioned a diuretic and, in particular, a saluretic such as, for example, a thiazide, a dihydrothiazide, a chlorosulfamide, a dihydrobenzofuran-2-carboxylic acid or a phenoxyacetic acid derivative. Examples of such compounds are N-(3'-chloro-4'-sulfamoylbenzamido)-2-methylindoline, ethacrynic acid and furosemide.

It is also possible to add an α-adrenolytic substance, a β-blocker, a calcium antagonist or a vascular dopaminergic receptor agonist.

The appropriate dosage can vary widely according to the patient's age and weight, the severity of the therapeutic indication and also the administration route. The preferred administration route is the buccal route, but the intravenous route is also perfectly suitable for the treatment of hypertension. Generally speaking, the unit dosage will preferably range between 0.05 and 20 mg.

The invention also relates to the processes for obtaining the compounds of formula (I), wherein a compound of formula (III):

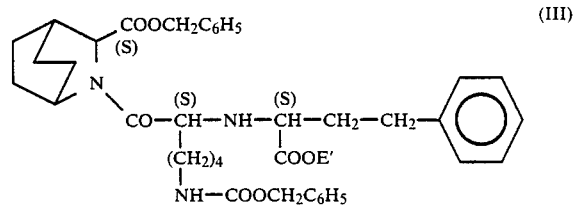

in which E' denotes a lower alkyl or benzyl group, is subjected to hydrogenation in the presence of a catalyst such as palladinized charcoal, to obtain:

the compound of formula (I) for which E=H, in the case where E' denotes a benzyl group, a compound of formula (I) for which E is a lower alkyl group, in the case where E' denotes a lower alkyl group, which compound can option ally be subjected to alkaline hydrolysis to obtain the compound of formula (I) for which E=H, it being possible, if so desired, for the compound of formula (I) thereby obtained to be salified with a therapeutically compatible inorganic or organic acid or base; the compound of formula (III) itself being obtained:

either by subjecting a 2-oxo-4-phenylbutyrate of formula (IV):

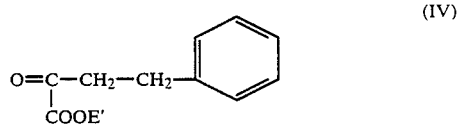

where E' has the same meaning as in the formula (III), to reductive amination in the presence of an alkali metal mixed hydride or an alkali metal mixed cyanohydride, such as sodium cyanoborohydride, with a lysine derivative in which the ε-amino and carboxyl groups are protected by suitable groups, such as tert-butyl (S)-N$^\epsilon$-benzyloxycarbonyllysinate of formula (V):

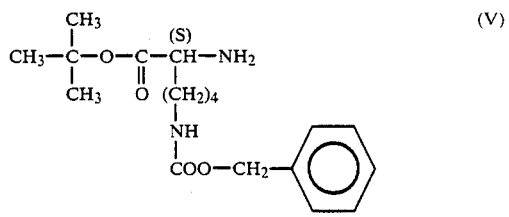

to obtain a compound of formula (VI):

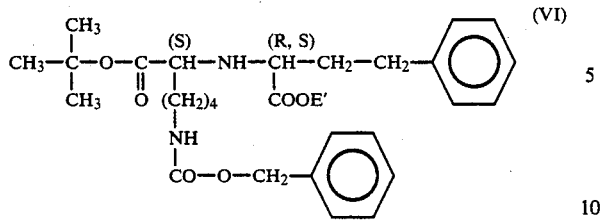

(VI)

in which E' has the same meaning as in the formula (III), the (S, R) and (S, S) isomers of which are isolated by a customary separation technique such as chromatography on a silica column, the (S, S) isomer thereby obtained then being subjected to a deprotection of the carboxylic acid group of the lysine in acid medium to obtain a compound of formula (VII):

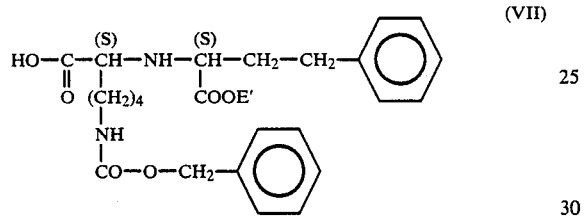

(VII)

in which E' has the meaning as in the formula (III), which is then condensed with a (3S)-2-azabicyclo[2.2.2]-octane-3-carboxylic acid ester, and preferably with the benzyl ester of formula (VIII):

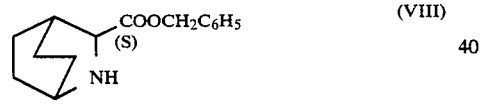

(VIII)

in the presence of a peptide coupling agent such as dicyclohexylcarbodiimide in the presence of hydroxybenzotriazole, to obtain a derivative of formula (III), or by coupling a (3S)-2-azabicyclo[2.2.2]octane-3-carboxylic acid ester and preferably the benzyl ester of the above formula designated (VIII), with a lysine derivative in which the α- and ε-amino groups are protected by suitable groups, such as (S)-N$^\alpha$-tert-butoxycarbonyl-N$^\epsilon$-benzyloxycarbonyllysine of formula (IX):

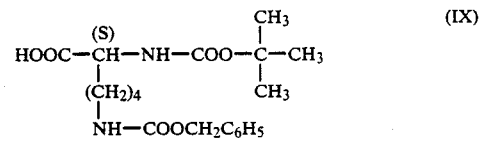

(IX)

in the presence of a peptide coupling agent such as dicyclohexylcarbodiimide in the presence of hydroxybenzotriazole, to obtain a compound of formula (X):

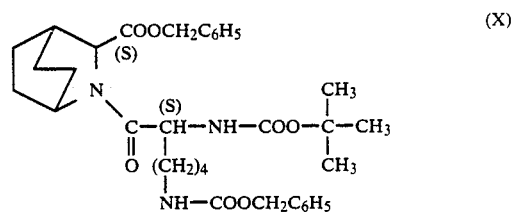

(X)

which is subjected to a deprotection of the α-amino group of the lysyl residue in acid medium, to obtain a compound of formula (XI):

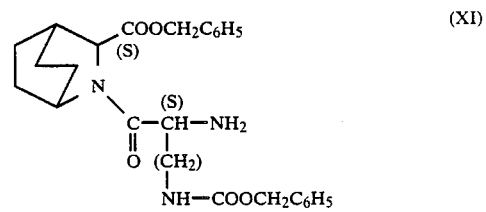

(XI)

which is subjected to reductive amination in the presence of an alkali metal mixed hydride or an alkali metal mixed cyanohydride, such as sodium cyanoborohydride, with a compound of formula (IV) designated above, to obtain the compound of formula (III) in racemic form (III, R, S):

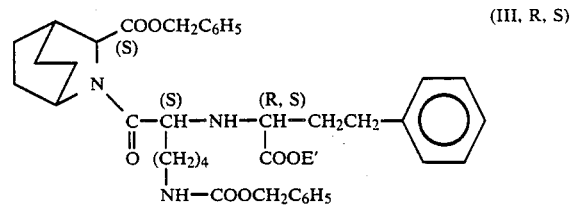

(III, R, S)

in which E' has the same meaning as in the formula (III), the (S, S, S) isomer of which is isolated by a customary separation technique such as chromatography on a silica column.

The compounds of formula (III) and their racemate of formula (III, R, S), as well as their addition salts with an inorganic or organic acid, are new and form part of the invention in the same manner as the compounds of formula (I).

The examples which follow illustrate the invention and in no way limit the latter.

The starting substances are known from the literature.

EXAMPLE 1:
(3S)-2-{(S)-N-[(S)-1-carboxy-3-phenylpropyl]lysyl}-3-carboxy-2-azabicyclo[2.2.2]octane hydrochloride

STAGE A:

Tert-butyl (S)-N$^\alpha$-[(S)-1-carbethoxy-3-phenylpropyl]-N$^\epsilon$-benzyloxycarbonyllysinate 10 g (0.0268 mol) of tert-butyl N$^\epsilon$-benzyloxycarbonyllysinate hydrochloride are dissolved in 150 cm$^3$ of anhydrous ethanol; 2.71 g (0.0268 mol) of triethylamine, 20.6 g (0.1 mol) of ethyl 2-oxo-4-phenylbutyrate and 20 g of 4Å molecular sieve are added. The mixture is stirred for one hour at 20° C. A solution of 1.68 g (0.0268 mol) of sodium cyanoborohydride in 20 cm³ of ethanol is then added in the course of 4 hours, after which stirring is continued for 18 hours at 20° C. The mixture is filtered and taken to dryness, the residue is redissolved in 200 cm³ of ethyl acetate and the solution is then washed twice with 100 cm³ of a 10% strength aqueous citric acid solution and then with water until the washing liquors are neutral. The mixture is dried over magnesium sulfate and evaporated. 28.7 g of an oil are collected, and this is purified by chromatography on silica gel (eluent: methylene chloride/acetone 95:5). After the removal of impurities and then the (S, R) isomer, 4.1 g of tert-butyl (S)-N$^\alpha$-[(S)-1-carbethoxy-3-phenylpropyl]-N$^\epsilon$-benzyloxycarbonyllysinate are collected, and used without further treatment in the following stage.

| Thin Layer chromatography: | support: | Si 60 F 254 |
|---|---|---|
| | solvent: | CH$_2$Cl$_2$: 95 |
| | | Acetone: 5 |
| | Rf: | 0.30 [(S, R) isomer |
| | | Rf: 0.40]. |

STAGE B:

(S)-N$^\alpha$-[(S)-1-Carbethoxy-3-phenylpropyl]-N$^\epsilon$-benzyloxycarbonyllysine hydrochloride 4.1 g of tert-butyl (S)-N$^\alpha$-[(S)-1-carbethoxy-3-phenylpropyl]-N$^\epsilon$-benzyloxycarbonyllysinate, obtained in the preceding stage, are dissolved in 100 cm³ of a 4N hydrochloric acid solution in dioxane, and the solution is left for 24 hours at 20° C. It is taken to dryness and solidified in ether. After drying in a dessicator, 3.8 g of (S)-N$^\alpha$-[(S)-1-carbethoxy-3-phenylpropyl]-N$^\epsilon$-benzyloxycarbonyllysine hydrochloride are recovered. Percentage composition:
calculated: C: 61.59; H: 6.96; N: 5.52; Cl: 6.99; found : C: 61.34; H: 7.26; N: 5.63; Cl: 6.93.

Infrared spectography: vs NH: 3360 cm$^{-1}$ vs CO: 1750 and 1690 cm$^{-1}$

STAGE C:

(3S)-2-{(S)-N$^\alpha$-[(S)-1-Carbethoxy-3-phenylpropyl]-N$^\epsilon$-benzyloxycarbonyllysyl}-3-benzyloxycarbonyl-2-azabicyclo[2.2.2]octane The (S)-N$^\alpha$-[(S)-1-carbethoxy-3-phenylpropyl]-N$^\epsilon$-benzyloxycarbonyllysine hydrochloride, obtained in the preceding stage, is coupled according to the technique of W. KÖNIG and R. GEIGER—Chem. Ber. (1970), 103, 788 with (3S)-2-azabicyclo[2.2.2]octane-3-carboxylic acid benzyl ester described in European Patent No. 0,051,020.

The (3S)-2-{(S)-N$^\alpha$-[(S)-1-carbethoxy-3-phenylpropyl]-N$^\epsilon$-benzyloxycarbonyllysyl}-3-benzyloxycarbonyl-2-azabicyclo[2.2.2]octane obtained, purified by chromatography on silica gel (eluent: ethyl acetate/cyclohexane 50:50) is used without further treatment in the following stage.

STAGE D:

(3S)-2-{(S)-N$^\alpha$-[(S)-1-Carbethoxy-3-phenylpropyl]-lysyl}-3-carboxy-2-azabicyclo[2.2.2]octane dihydrochloride 2.8 g of (3S)-2-{(S)-N$^\alpha$-[(S)-1-carbethoxy-3-phenylpropyl]-N$^\epsilon$-benzyloxycarbonyllysyl}-3-benzyloxycarbonyl-2-azabicyclo[2.2.2]octane, obtained in the preceding stage, are dissolved in 100 cm³ of ethanol; 0.2 g of palladinized charcoal (10% palladium) is added and the mixture is hydrogenated for 18 hours at 20° C. under a hydrogen pressure of 3 kg/cm².

The catalyst is filtered off, 10 cm³ of a 4N hydrochloric acid solution in ether are added, and the mixture is taken to dryness. The residue is taken up with ethyl acetate and the mixture filtered and dried in a dessicator. 1.75 g of (3S)-2-{(S)-N$^\alpha$-[(S)-1-carbethoxy-3-phenylpropyl]lysyl}-3-carboxy-2-azabicyclo[2.2.2]octane dihydrochloride are obtained (yield: 80%).

Percentage composition: calculated : C: 57.14; H: 7.56; N: 7.69;Cl: 12.97;
found : C: 56.76; H: 7.31; N: 7.76; Cl: 12.97.

Spectral study: Infrared spectrometry vCO: 1650 and 1740 cm$^{-1}$. Mass spectrometry: DCI spectrum (NH$_3$).

M/Z: 474: [M + H]$^\oplus$
456: [M + H − H$_2$O]$^\oplus$

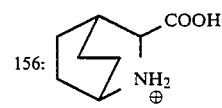

STAGE E:

(3S)-2-{(S)-N$^\alpha$-[(S)-1-Carboxy-3-phenylpropyl]lysyl}-3-carboxy-2-azabicyclo[2.2.2]octane dihydrochloride 1.75 g (2.75 mmol) of (3S)-2-{(S)-N$^\alpha$-[(S)-1-carbethoxy-3-phenylpropyl]lysyl}-3-carboxy-2-azabicyclo[2.2.2]octane dihydrochloride, obtained in the preceding stage, are dissolved in 120 cm³ (1.2 mmol) of 0.1N sodium hydroxide. After 48 hours at room temperature, the solution is neutralized with 12 cm³ of 1N hydrochloric acid, and then taken to dryness. The residue is redissolved in 30 cm³ of anhydrous isopropanol and the insoluble sodium chloride removed by filtration. The mixture is taken to dryness and the operation is repeated. The residue is taken up with water and the mixture filtered on a 0.22 μm millipore filter and lyophilized. 1.2 g of (3S)-2-{(S)-N$^\alpha$-[(S)-1-carboxy-3-phenylpropyl]lysyl}-3-carboxy-2-azabicyclo[2.2.2]octane dihydrochloride are recovered.

Rotary power:
[$\alpha$]$_D^{21°\ C.}$ = 18 2≧'(c: 1% pyridine).

Spectral study: Infrared spectrometry: vCO acid 1710 cm$^{-1}$; vCO 1640 cm$^{-1}$. Mass spectrometry: DCI.
M/Z: 446: [M−H]$^\oplus$. 428: [M+H−H$_2$O]$^\oplus$.

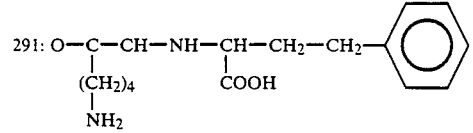

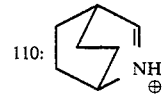

Nuclear magnetic resonance spectrometry: Solvent D$_2$O (T=301° K.) δ$^1$H in ppm TMS (external reference);

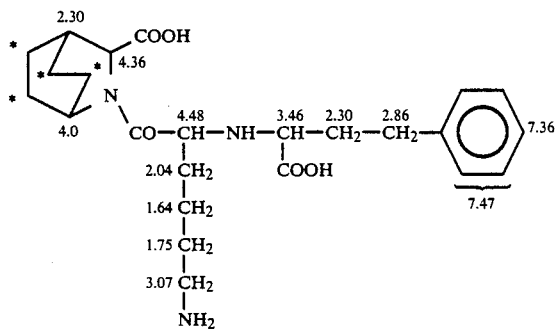

*complex: 1.91 to 1.64 ppm

δ$^{13}$C in ppm TMS (external reference):

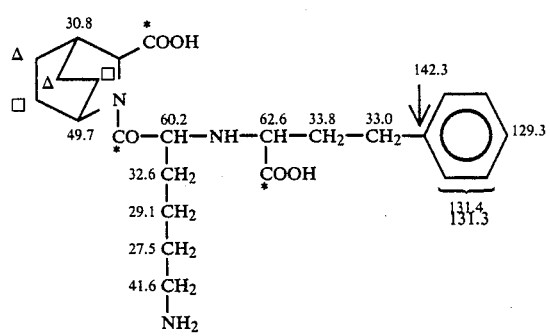

*176.0; 173.7; 169.1
Δ 23.2; 22.2
□ 28.2; 26.3.

EXAMPLE 2: (3S)-2-{(S)-N-[(S)-1-ETHOXYCARBONYL-3-PHENYLPROPYL]LYSYL}-3-CARBOXY-2-AZABICYCLO[2.2.2]OCTANE DIHYDROCHLORIDE

STAGE A:

(3S)-2-[(S)-N$^α$-Tert-butoxycarbonyl-N$^ε$-benzyloxycarbonyllysyl]-3-benzyloxycarbonyl-2-azabicyclo[2.2.2]octane (S)-N$^α$-Tert-butoxycarbonyl-N$^ε$-benzyloxycarbonyllysine is coupled according to the technique of W. KÖNIG and R. GEIGER—Chem. Ber. (1970), 103, 788 with (3S)-2azabicyclo[2.2.2]octane-3-carboxylic acid benzyl ester, described in European Patent No. 0,051,020.

The (3S)-2-[(S)-N$^α$-tert-butoxycarbonyl-N$^ε$-benzyloxcycarbonyllsyl]-3-benzyloxycarbonyl-2-azabicyclo[2.2.2]octane obtained, purified by chromatography on silica gel, is used without further treatment in the following stage.

STAGE B:

(3S)-2-[(S)-N$^ε$-Benzyloxycarbonyllysyl]-3-benzyloxycarbonyl-2-azabicyclo[2.2.2]octane Using the method of deprotection with trifluoroacetic acid in anhydrous methylene chloride, described by B. GUTTE and K. B. MERRIFIELD (J. Am. Chem. Soc. 1969, 91, 501), a quantitative yield of (3S)-2-[(S)-N$^ε$-benzyloxycarbonyllysyl]-3-benzyloxycarbonyl-2-azabicyclo[2.2.2]octane is obtained from the (3S)-2-[(S)-N$^α$-tert-butoxycarbonyl-N$^ε$-benzyloxycarbonyllysyl]-3-benzyloxycarbonyl-2-azabicyclo[2.2.2]octane prepared in the preceding stage.

STAGE C:

(3S)-2-{(S)-N$^α$-[(S)-1-Carbethoxy-3-phenylpropyl]-N$^ε$-benzyloxycarbonyllysyl}-3-benzyloxycarbonyl-2 azabicyclo[2.2.2]octane The (3S)-2-[(S)-N$^ε$-benzyloxycarbonyllysyl]-3-benzyloxycarbonyl-2-azabicyclo[2.2.2]octane, obtained in the preceding stage, is subjected to reductive amination in the presence of sodium cyanoborohydride with ethyl 2-oxo-4-phenylbutyrate, to obtain, after purification on silica gel and removal of the (S, S, R) isomer, (3S)-2-{(S)-N$^α$-[(S)-1-carbethoxy-3-phenylpropyl]-N$^ε$-benzyloxycarbonyllysyl}-3-benzyloxycarbonyl-2-azabicyclo[2.2.2]octane, which is used without further treatment in the following stage.

STAGE D:

(3S)-2-{(S)-N$^α$-[(S)-1-Carbethoxy-3-phenylpropyl]-lysyl}-3-carboxy-2-azabicyclo[2.2.2]octane dihydrochloride Starting with the product obtained in the preceding stage, and working in the same manner as described in Example 1 - Stage D, (3S)-2-{(S)-N$^α$-[(S)-1-Carbethoxy-3-phenylpropyl]lysyl}-3-carboxy-2-azabicyclo[2.2.2]octane dihydrochloride is obtained.

EXAMPLE 3: PHARMACOLOGICAL STUDY OF THE COMPOUND OF THE INVENTION FOR WHICH E=H

The compound of the invention for which E=H was tested by oral administration on unanesthetized dogs.

The arterial blood pressure of the dogs was measured with a pressure gauge ("Statham P23 Db") after catheterization of the aorta via the femoral artery. The recording is carried out with a recording apparatus ("Brush 400").

Angiotensin I and angiotensin II are injected into the animals intravenously at doses of 0.5 and 0.10 γ/kg, respectively. A dose/activity curve is established for each of these hormones. The compound according to the invention for which E=H is then administered orally at a dose of 1 mg/kg. A second dose/activity curve is then established for angiotensin I and for angiotensin II after administration of the test product.

It is found that the compound of the invention for which E=H possesses a rapid, intense and prolonged activity at a dose of 1 mg.kg$^{-1}$, this being the case when it is administered orally, which distinguishes it clearly from the compounds of the prior art. A quarter of an hour after the oral administration of one mg.kg$^{-1}$ of the compound of the invention in dogs, the percentage inhibition of the converting enzyme is 80%. It is in the region of 100%, 30 minutes after administration, and remains greater than 70%, six hours after administration.

In comparison with the derivatives of European Patent No. 0,051,020, it is apparent that the result is surprising when the speed with which an intense activity is obtained after the oral administration of a dose of 1 mg.kg$^{-1}$, and the period during which this activity is maintained, are considered: a speed of action of this kind had been obtained for the compounds of European Patent No. 0,051,020 only after intravenous administration, and it was possible to observe a comparable duration of action only after the administration of a markedly higher dose. The novel structure of the compound of the present invention hence confers very advantageous activity, at a level which is surprising compared with the compounds of the prior art.

EXAMPLE 4: PHARMACEUTICAL COMPOSITION

Tablet: Preparation formula for 1000 tablets containing a 2-mg dose of active principle. (3S)-2-{(S)-N$^\alpha$-[(S)-1-Carboxy-3-phenylpropyl]lysyl}-3-carboxy-2-azabicyclo[2.2.2]octane dihydrochloride: 2 g
Hydroxypropylcellulose: 2 g
Wheat starch: 10 g
Lactose: 100 g
Magnesium stearate: 3 g
Talc: 3 g

We claim:

1. The compounds of formula (I):

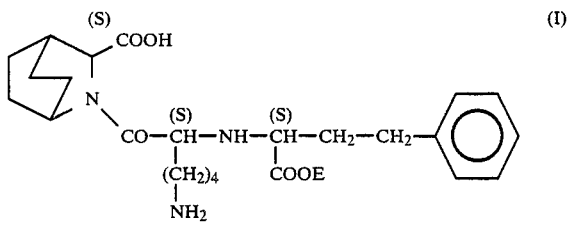

in which E is a hydrogen atom or a lower alkyl radical, as well as their addition salts with a pharmaceutically acceptable base or acid.

2. A compound as claimed in claim 1 in which E denotes a hydrogen atom, namely (3S)-2-{(S)-N$^\alpha$-[(S)-1-carboxy-3-phenylpropyl]lysyl}-3-carboxy-2-azabicyclo2.2.2]octane, as well as its addition salts with a pharmaceutically acceptable base or acid.

3. A compound as claimed in claim 1 in which E denotes an ethyl group, namely (3S)-2-{(S)-N$^\alpha$-[(S)-1-ethoxycarbonyl-3-phenylpropyl]lysyl}-3-carboxy-2-azabicyclo[2.2.2]octane, as well as its addition salts with a pharmaceutically acceptable base or acid.

4. A pharmaceutical composition useful in antihypertensive therapy containing, as active principle, an antihypertensive amount of a compound as claimed in claim 1, in combination with one or more pharmaceutically acceptable, non-toxic inert vehicles or excipients.

5. A pharmaceutical composition useful in anti-hypertensive therapy containing, as active principle, an antihypertensive amount of the compound as claimed in claim 2, in combination with one or more pharmaceutically acceptable, non-toxic inert vehicles or excipients.

6. A method for treating a living animal body afflicted with hypertension or a related ailment selected from the group consisting of cardiac insufficiency, secondary hyperaldosteronism, primary and secondary pulmonary hypertension, glaucoma, renal insufficiency, renal vascular hypertension, peripheral vascular disorders selected from migraine, Raynaud's disease, atherosclerosis, thrombosis, arteritis of the lower limbs, cirrhosis, and ascites, comprising the step of administering to the said living animal body an effective amount of a compound of claim 1 or a pharmaceutical composition of claim 4.

* * * * *

UNITED STATES PATENT AND TRADEMARK OFFICE
CERTIFICATE OF CORRECTION

PATENT NO. : 4,959,372

DATED : Sep. 25, 1990

INVENTOR(S) : Michel Vincent, Georges Remond, Michel Laubie

It is certified that error appears in the above-identified patent and that said Letters Patent is hereby corrected as shown below:

```
Title Page, [73] Assignee:  "Adir Et lie," should read
   -- Adir Et Cie, --.
Column 4, line 5; "a 8-blocker," should read -- a β-blocker, --.
Column 7, approximate line 40; "cm⁻¹" should read -- cm⁻¹. --.
Column 8, line 47; "=18 2≧' (" should read -- =18.2° ( --.
Column 8, line 50; "[M-H]⊕ should read -- [M+H]⊕ --.
Column 9, line 56/57; "benzyloxcycarbonyllsyl]" should read
   -- benzyloxycarbonyllysyl] --.
Column 10, line 44; "0.5" should read -- 0.15 --.  (R A 3-5-90, P 1)
Column 12, line 6/7; "-azabicyclo2.2.2]" should read
   -- -azabicyclo-[2.2.2] --.
```

Signed and Sealed this

Seventh Day of April, 1992

*Attest:*

HARRY F. MANBECK, JR.

*Attesting Officer*     *Commissioner of Patents and Trademarks*